(12) United States Patent
Nardini et al.

(10) Patent No.: US 8,933,204 B2
(45) Date of Patent: Jan. 13, 2015

(54) PROCESS FOR THE INDUSTRIAL-SCALE PURIFICATION OF GAMMA GLOBULINS FROM HUMAN PLASMA FOR INDUSTRIAL APPLICATIONS

(75) Inventors: Claudia Nardini, Lucca (IT); Andrea Morelli, Lucca (IT); Claudio Farina, Pisa (IT); Sabrina Esposito, Ghivizzano (IT); Alessandra Lazzarotti, Massa (IT); Arianna Petrucci, Barga (IT)

(73) Assignee: Kedrion S.p.A., Barga (IT)

( * ) Notice: Subject to any disclaimer, the term of this patent is extended or adjusted under 35 U.S.C. 154(b) by 0 days.

(21) Appl. No.: 13/519,368

(22) PCT Filed: Dec. 28, 2010

(86) PCT No.: PCT/IB2010/056093
§ 371 (c)(1),
(2), (4) Date: Aug. 21, 2012

(87) PCT Pub. No.: WO2011/080698
PCT Pub. Date: Jul. 7, 2011

(65) Prior Publication Data
US 2012/0316323 A1 Dec. 13, 2012

(30) Foreign Application Priority Data
Dec. 28, 2009 (IT) .............................. FI2009A0273

(51) Int. Cl.
| | | |
|---|---|---|
| *A23J 1/00* | (2006.01) | |
| *C07K 1/00* | (2006.01) | |
| *C07K 14/00* | (2006.01) | |
| *C07K 17/00* | (2006.01) | |
| *C07K 16/06* | (2006.01) | |
| *C07K 1/18* | (2006.01) | |
| *C07K 1/34* | (2006.01) | |

(52) U.S. Cl.
CPC ............... *C07K 16/065* (2013.01); *C07K 1/18* (2013.01); *C07K 1/34* (2013.01); *C07K 2317/21* (2013.01)
USPC ............................ 530/412; 530/414; 530/416

(58) Field of Classification Search
None
See application file for complete search history.

(56) References Cited

U.S. PATENT DOCUMENTS

| | | | | |
|---|---|---|---|---|
| 5,593,675 | A | * | 1/1997 | Hodler et al. ............... 424/130.1 |
| 7,888,098 | B2 | * | 2/2011 | Richter et al. ................ 435/239 |
| 2007/0292442 | A1 | * | 12/2007 | Wan et al. .................. 424/176.1 |

FOREIGN PATENT DOCUMENTS

| | | | |
|---|---|---|---|
| EP | 0440483 A2 | 8/1991 | |
| GB | 1344340 | 1/1974 | |
| WO | WO8905157 A1 * | 6/1989 | ........... A61K 39/395 |

OTHER PUBLICATIONS

Kreil et al. "Removal of small nonenveloped viruses by antibody-enhanced nanofiltration during the manufacture of plasma derivatives" Transfusion, 46, 2006, pp. 1143-1151.*
Ip.com Prior Art Database Technical Disclosure, "Purification of a monoclonal antibody on Capto S" IPCOM000134350D, Mar. 3, 2006, pp. 1-6.*
Tornoe et al.; "Pilot Scale Purification of Human Monoclonal IgM (COU-1) for Clinical Trials"; Journal of Immunological Methods 205 (1997) 11-17.
McCarthy et al.; "Rapid Purification and Monitoring of Immunoglobulin M From Ascites by Perfusion Ion-Exchange Chromatography"; Journal of Chromatography A, 743 (1996) 163-170.
Yang et al.; Influence of Column Type and Chromatographic Conditions on the Ion-Exchange Chromatography of Immunoglobulins; Journal of Chromatography A, (1996) 171-180.
Stucki et al.; "Characterisation of a Chromatographically Produced Anti-D Immunoglobulin Product"; Journal of Chromatography B, 700 (1997) 241-248.
Written Opinion of the International Searching Authority dated Jun. 28, 2012 for International Application No. PCT/IB2010/056093.

* cited by examiner

*Primary Examiner* — Daniel E Kolker
*Assistant Examiner* — James Rogers
(74) *Attorney, Agent, or Firm* — Abelman, Frayne & Schwab

(57) ABSTRACT

The invention relates to a novel, industrial-scale process for the purification of gamma-immunoglobulins (IgG) starting from plasma or fractions thereof. The method involves two chromatographic steps, i.e. a cation exchange capture chromatography, and then a polishing anion exchange chromatography, ensuring a highly purified end product, which contains no aggregates, and high yields. The process also involves a virus inactivation step by means of a solvent/detergent treatment to inactivate the viruses with a lipid envelope, and a virus removal step by nanofiltering to ensure the removal of the non-enveloped viruses.

3 Claims, 3 Drawing Sheets

US 8,933,204 B2

PROCESS FOR THE INDUSTRIAL-SCALE PURIFICATION OF GAMMA GLOBULINS FROM HUMAN PLASMA FOR INDUSTRIAL APPLICATIONS

CROSS REFERENCE TO RELATED APPLICATIONS

This application is a National Phase of PCT/IB2010/056093, filed 28 Dec. 2010, which claims priority from Italian Application No. FI 2009A000273, filed 28 Dec. 2009, both of which are incorporated herein by reference.

FIELD OF THE INVENTION

The present invention refers to the field of plasma derivatives, and to immunoglobulins (IgG) in particular, and specifically to a process for the production of gamma globulins for intravenous administration (IVIG).

State of the Art

IVIG are the plasma derivative in greatest demand on the world market: in 2008 the market for IVIG reached approximately 82 metric tons (including 37 in the USA, 21 in Europe and 17 in Asia) with a tendency to grow at a rate of approximately 7% a year (the predicted demand in 2012 is for 108 t).

IVIG are used in a number of clinical applications for the treatment of primary or acquired immunodeficiencies, and to treat infectious and autoimmune diseases. There has also been a marked increase in the number of studies focusing on further therapeutic uses of IVIG.

The decline in adverse reactions thanks to the greater tolerability of the IVIG available on the market has extended the therapeutic applications of IVIG and consequently led to an increasing use of this plasma derivative. The greater demand for this drug is often not satisfied, however, due to its inadequate market availability.

The industrial process commonly used to purify IgG is a modified and optimised version of the original method devised by Cohn, which dates back to the 1940s and is based on the cold fractionated precipitation of plasma proteins. After progressive additions of ethanol under controlled conditions of ionic force, pH and temperature, this plasma fractionation process obtains enriched or concentrated fractions of proteins for therapeutic applications (coagulation factors, albumin, immunoglobulin, antithrombin III). Applying Cohn's fractionation, IgG are obtained from fractions II+III.

The limited availability of IVIG on the world market reflects the low yields (averaging 3.5-4.2 g of IgG per kg of plasma) of currently-used production processes, which are modified and optimised versions of Cohn's original method. The end product represents a mean 30% of the IgG existing in the original plasma pool. This explains why the major manufacturing companies are concentrating on developing a more advanced production process, which includes chromatographic purification steps, characterised in an increase in the yield by comparison with the traditional process and capable of providing a product with guaranteed of safety, efficacy and tolerability features.

The new method offers further advantages over ethanol-based fractionation, the first of which is a marked reduction in the use of ethanol and the potential elimination of the distilling system, with the consequent total or partial elimination of the centrifugation steps (meaning a less noisy, cleaner environment with no aerosol generation, a lower mechanical risk, a less bulky instrumentation), the partial or total elimination of the filtering stages obtained by adding adjuvants (and a consequently "cleaner" process), and a reduction in the process volumes due, in Cohn's method, to the plasma being diluted before undergoing ethanolic precipitation. In addition, the blander, buffered process conditions enable a marked reduction in the risk of the proteins being denatured.

The use of chromatographic methods for the purification of IVIG has already been explored: in particular, cation and anion exchange chromatography, variously combined in separate steps or in series, are described in patented methods for purifying IgG from plasma or fractions thereof.

In the majority of the patented methods, anion exchange chromatography is used in negative mode, i.e. conditions are used to enable the binding of the contaminant proteins, e.g. IgA, IgM, albumin, fibrinogen, transferrin, while the IgG are recovered in the non-adsorbed product.

US2007049733 describes a method for purifying IgG starting from fresh frozen plasma, which involves a cation exchange chromatography capture step on a weak exchanger (CM 650 Toyopearl), then a double virus activation, anion exchange chromatography on QAE-550 C Toyopearl resin, conducted in negative mode, and a final nanofiltering step. Before the chromatographic separation steps, the method involves two precipitations with sodium citrate. A paste is obtained from the first precipitation, from which Factor VIII, Factor IX, von Willebrand factor and fibrinogen are purified. The supernatant deriving from the first precipitation undergoes a second precipitation to obtain a supernatant containing albumin and a paste from which the IgG are purified. This paste is solubilised in water and undergoes diafiltration to remove the sodium citrate.

Both of these precipitation steps involve the use of filtering adjuvants and the IgG are also precipitated, which implies a solubilisation step to remove the filtering adjuvants.

WO9805686 describes a method for purifying IgG on an industrial scale starting from plasma, supernatant I or fractions II+III. The lipoproteins are preferably removed from the initial sample using colloidal silica and euglobins, depending on its complexity. This is followed by two chromatographic steps, the first in an anion exchanger (DEAE-Sepharose FF) at a pH of 5.2, the on a macroporous anion exchange resin (MacroPrepHQ, MacroprepQ, PorosQ, QHyper DM) at a pH of 6.0-6.6. Both the chromatographic steps are conducted in negative mode and the second chromatography, in particular, ensures a good charging capacity, absorbing the contaminant proteins, and transferrin in particular.

In patent No. U.S. Pat. No. 6,307,028 B1 (2001) (11) for the purification of IgG from plasma or fractions thereof, e.g. fractions II+III, there are two chromatographic steps, with an anion exchange in negative mode, after pretreatment with caprylic acid. In the first step, a strong anion exchanger is used to bind the IgA, in the second step, a weak anion exchanger is used to bind the IgM.

The methods claimed in U.S. Pat. No. 6,093,324 (2000) and U.S. Pat. No. 6,307,028 B1 (2001) would seem to be more suitable for partially purified intermediates than for plasma, unless large quantities of resin are to be used in industrial-scale applications.

US2001051708 describes a method for purifying IgG starting from standard or hyperimmune plasma, or from plasma fractions enriched with IgG, that involves a pretreatment with a precipitating agent (PEG, caprylic acid, ammonium sulphate) to remove lipoproteins, contaminant proteins, aggregates and viruses. This is followed by anion exchange chromatography (DEAE Sepharose Fast Flow) in negative mode in series with cation exchange chromatography (CM Sepharose Fast Flow) to bind the IgG. This procedure is repeated a second time, after pretreatment with a solvent/detergent (S/D), to refine the grade of purity and remove the virus-inactivating components. The method described in this patent involves a step for removing the lipoproteins and numerous chromatographic steps, making it scarcely applicable on an industrial scale.

In WO9429334, IgG are purified, starting from plasma, by anion exchange chromatography conducted in negative mode (DEAE-Trisacryl) coupled with a cation exchange chromatography (CM-Trisacryl), after virus activation by means of a S/D mixture.

WO02092632 describes a method for purifying IgG from plasma, or fractions of plasma, by means of a single chromatographic step in an anion exchanger, after pretreatment with caprylic acid and virus inactivation with a S/D mixture. In this case, the anion exchanger is used in alkaline conditions to bind the IgG and eliminate the virus-inactivating components. The IgG are collected by changing the pH, while the IgA and IgM are eliminated in subsequent steps and separated by increasing the ionic force.

Again in WO9429334 and WO02092632 the claimed method seems more suitable for use with partially purified intermediates unless large quantities of resin are used, and it fails to take the subsequent purification of albumin into account, which is complicated somewhat by the fact that it remains bound to the resin used in the first chromatographic step.

The object of the present invention is an alternative process applicable on an industrial scale to the isolation of IgG from plasma or plasma fractions with a high yield.

Definitions and Abbreviations

IgG=gamma globulins
IVIG=gamma globulins for intravenous injection
IgM=M immunoglobulins
IgA=A immunoglobulins
S/D=solvent/detergent
PTC=prothrombin complex
PEG=polyethylene glycol

SUMMARY OF THE INVENTION

The present invention achieves the aforementioned object by means of a process for the industrial production of IVIG, using plasma or intermediate plasma fractions enriched with IgG, and preferably the cryosupernatant or supernatant from Cohn's fraction I, as the raw material. Said process comprises two chromatographic steps: the first chromatographic step consists of a IgG "capture" step on a strong cation exchanger; the second consists of a "polishing" step conducted on a strong anion exchanger, i.e. characterised by quaternary ammonium groups.

The cation exchanger in question belongs to the class of strong exchangers with the $SO_3^-$ functional group. Resins in the Capto family, e.g. Capto S (GEHealthcare), and in the Gigacap family, e.g. Gigacap S 650 M (Toyopearl), may be used. The cation exchange chromatography capture step is conducted in conditions designed to enable the binding of the IgG.

The resin used for the polishing chromatography step belongs to the family of tentacular Fractogels (Merck) and is used in pH and conductivity conditions designed to enable the binding of both the IgG and the contaminant proteins (IgA, IgM and transferrin), The method according to the invention offers the following advantages over the previously-mentioned patents:

the starting material does not require any preliminarily treatment to remove the lipoproteins;

the decision to bind the IgG rather than the contaminant proteins derives from the fact that, because the content of target proteins is smaller than that of the contaminant proteins, this enables the dimensions of the chromatographic column to be kept as small as possible in industrial-scale applications;

the polishing chromatography serves the dual purpose of removing the solvent and detergent used for the virus inactivation step, optionally included between the two chromatographies, and also of resolving between the IgG and the contaminant proteins, achieved by means of a selective elution step. Said virus inactivation step, optionally included between the two chromatographies and conducted by means of a solvent-detergent treatment, enables the viruses with a lipid envelope to be inactivated;

the process also optionally and preferably involves a nanofiltering step, which ensures the removal of the non-enveloped viruses and the formulation of the end product with a pH of 4, a condition that guarantees a greater stability of the product. The treatment and the pH 4 constitute a further virus inactivation step. The process as a whole guarantees higher yields (5.1 g of IgG per kg of plasma) than the classic Cohn method and an extremely purified product, with no degradation products.

The process as claimed herein for the production of IVIG does not interfere significantly with the processes for purifying other plasma proteins.

In fact, the starting material is not fresh frozen plasma, but preferably the supernatant of fraction I deriving from the Cohn fractionation method, which has the advantage of not affecting the plasma thawing and the recovery of the cryopaste fundamental to the purification of FVIII, von Willebrand factor and fibrinogen. Starting from the supernatant I also means that the process according to the invention does no interfere with the extraction of PTC and antithrombin III, and the use of ethanol is relegated to the precipitation of fraction I alone.

The fraction not bound by the first IgG capture step, when all the albumin is still contained in the processed plasma, has characteristics that make it readily suitable for re-inclusion in the process for albumin purification by ethanolic precipitation.

The invention concerns a novel process for the purification and industrial production of human gamma-immunoglobulins formulated in a manner suitable for intravenous administration, starting from plasma or plasma fractions.

DETAILED DESCRIPTION OF THE INVENTION

Figure 1:
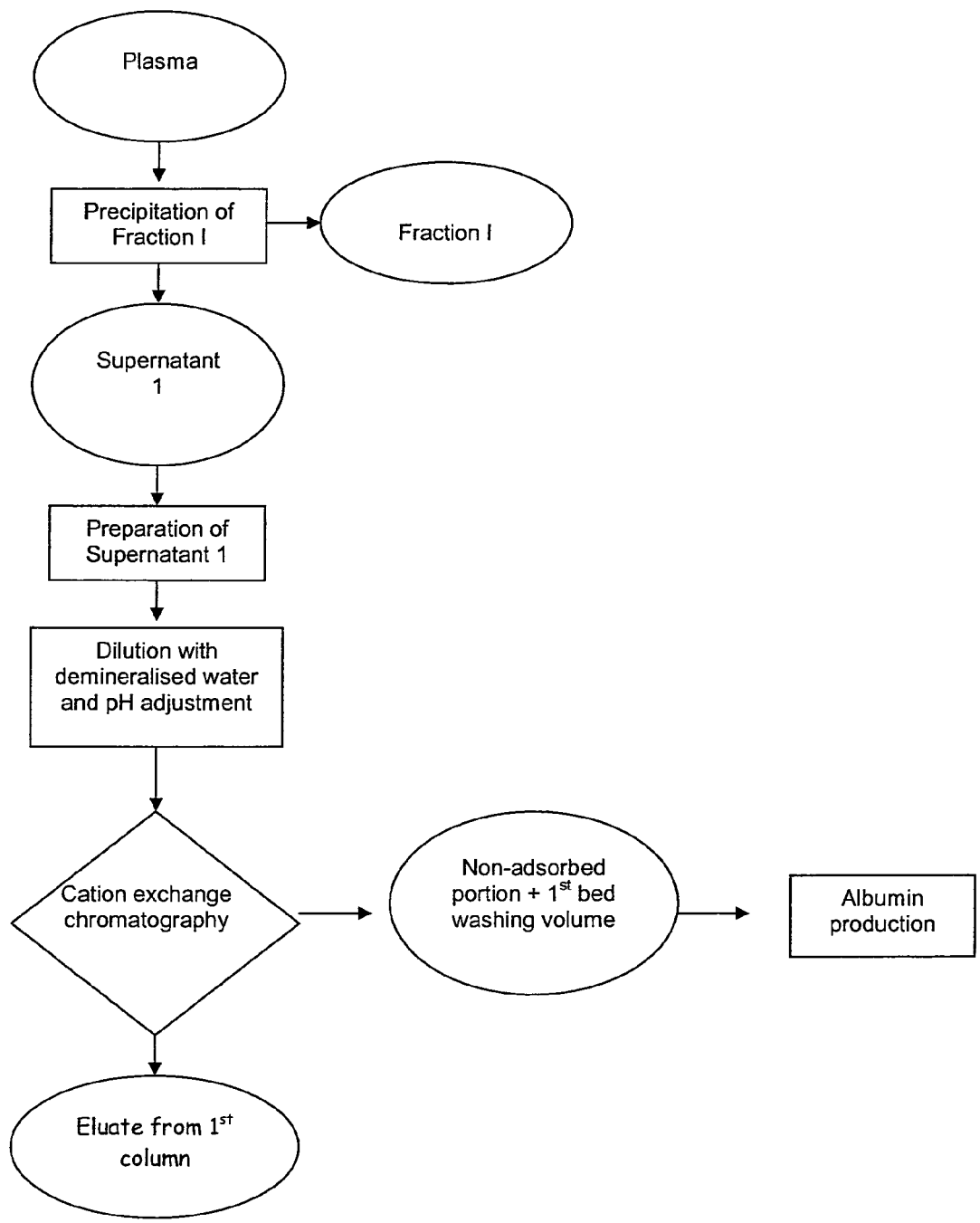
FIG. 1 shows the flowchart of a preferred embodiment of the method according to the invention, from the raw material up to the production of a solution of IgG of intermediate purity, after elution from the first "capture" chromatographic step on a strong cation exchange resin.

In the present invention, the cryosupernatant or supernatant I deriving from the Cohn fractionation method are preferred as the starting material. After correcting the pH to 5.4-5.7, and preferably 5.6, the starting material is diluted with water to obtain a conductivity in the range of 3.5-4.5 mS/cm, and preferably 4 mS/cm.

After pH correction and pre-dilution, the sample is filtered through a depth filter and then through a clarifying filter; then the filtered sample is fractionated by cation exchange chromatography.

The resin used for the first chromatography belongs to the Capto (GE Healthcare) or Gigacap (Toyopearl) families, characterised by the —$SO_3^-$ functional group, which ensure a high charging capacity and high selectivity. Among the many tested, these types of resin were chosen because they guarantee a high IgG charging capacity. In the experimental conditions adopted, almost all of the IgG contained in the processed sample bind to the cation exchanger and the bound proportion is subsequently eluted in a single step by increasing the ionic force.

The unbound fraction after capture chromatography step is suitable for use as a raw material for the purification of albumin.

The cation exchange column is preferably conditioned with 25-75 mM buffer, better still with 50 mM sodium acetate, at a pH in the range of 5.4-5.7, and preferably 5.6. The column is charged with 20-60 mg of IgG per ml of resin, and preferably 40 mg of IgG per ml of resin. After charging, the column is washed with at least 7 bed volumes of 50 mM buffer at a pH in the range of 5.4-5.7, and preferably 5.6. The non-adsorbed portion and the first washing bed volume are collected and used for the purification of albumin.

In the conductivity and pH conditions adopted for column conditioning and washing, and to prepare the starting material, the percentage of IgG binding to the chromatographic resin is in the range of 80% to 85% of the initial charge, while all the albumin and transferrin are eluted in the non-adsorbed portion and the first washing bed volume.

The IgG are eluted by increasing the ionic force and washing the chromatographic resin with buffer characterised by a sodium chloride concentration in the range of 0.25 M to 1 M, and preferably with a NaCl concentration of 0.6 M, and a pH in the range of 5.4 to 5.7, and preferably 5.6.

The product, which is a solution of IgG of intermediate purity, is eluted in a single cation exchange chromatography step, then preferably filtered through a clarifying filter before it is dialysed by cross flow filtering to replace the buffer used to elute the chromatographic capture resin with a 10-30 mM buffer, preferably Tris 20 mM, pH 9.0±0.5, NaCl 8-10 mM (preferably 9 mM), and concentrated to a protein concentration level in the range of 15-25 mg/ml, and preferably 20 mg/ml. For cross flow filtering, the modules used have a molecular cut-off of 50 or 100 KDa.

Then the concentrated product preferably undergoes a filtering step through a clarifying filter, followed by filtering through a sterilising grade filter.

The product, with a protein concentration in the range of 25-30 mg/ml, then undergoes a virus activating step, involving treatment with a solvent/detergent mixture (1% Triton-X100 and 0.3% TnBP). The protein solution is agitated under controlled temperature conditions in the range of 24° C. to 28° C., and preferably 25° C., for a contact period in the range of 6-10 hours, and preferably 8 hours.

After being treated with the solvent/detergent mixture, and filtered through a clarifying filter, the product is further purified by ion exchange chromatography on a resin with quaternary ammonium groups as the exchanger groups, e.g. Fractogel TMAE, with a protein charge in the range of 20-60 mg of protein per ml of resin, and preferably 50 mg/ml. The chromatography resin is conditioned with 10-30 mM buffer, preferably Tris-HCl 20 mM, pH 9.0±0.5, and NaCl 8-10 mM, preferably 9 mM. After charging the product, the resin is washed extensively with 10-30 mM buffer, preferably Tris-HCl 20 mM, pH 9.0±0.5, and NaCl 8-10 mM, preferably 9 mM, to ensure the reduction of the Triton X-100 and TnBp to the values specified for the end product. In the conductivity and pH conditions adopted for conditioning and washing the anion exchange chromatography resin and for preparing the solution of IgG of intermediate purity submitted to S/D treatment, the IgG and contaminant proteins bind to the resin. The IgG are separated from the contaminants by selective elution.

The IgG are eluted either by increasing the ionic force or by changing the pH.

When they are eluted by increasing the ionic force, a buffer is used with a conductivity in the range of 9.5 to 10.5 mS/cm and a pH of 9.0±0.5. The IgG are retrieved with a yield of at least 80% and the purity of at least 95%, preferably 98%. The IgA and IgM levels come within the limits specified for IVIG produced using the currently-adopted method.

When the elution is done by changing the pH, a sodium phosphate, sodium acetate or MES buffer is used with a conductivity in the range of 1 to 1.5 mS/cm, preferably 1.2 mS/cm, and a pH in the range of 6-7, preferably 6.2. The IgG are retrieved with a yield of at least 95% and a purity of at least 95%, preferably 98%. The IgA and IgM levels come within the limits specified for IVIG produced according to the currently-adopted method.

The solution of IgG with a high purity obtained by anion exchange chromatography is filtered with a clarifying filter and then pre-formulated by cross flow filtering, using modules with a molecular cut-off of 50 or 100 KDa, in glycine 0.25 M, NaCl 9 mM, pH 6, and is concentrated to a protein concentration in the range of 25-35 mg/ml, and preferably 30 mg/ml.

The high-purity IgG solution is dialysed and concentrated to 30±5 mg of proteins/ml, after correcting the pH to 4, then pre-filtered through a sterilising grade filter with a porosity of 0.1 μm, and filtered on a virus grade filter with a porosity of 20 nm.

The nanofiltered product is further concentrated to a final protein concentration of 90-110 g/L (preferably 100 g/L) by cross flow filtering on modules with a molecular cut-off of 100 KDa.

The final solution containing 10% of IgG subsequently undergoes sterilising grade filtering before bottling.

Figure 2:
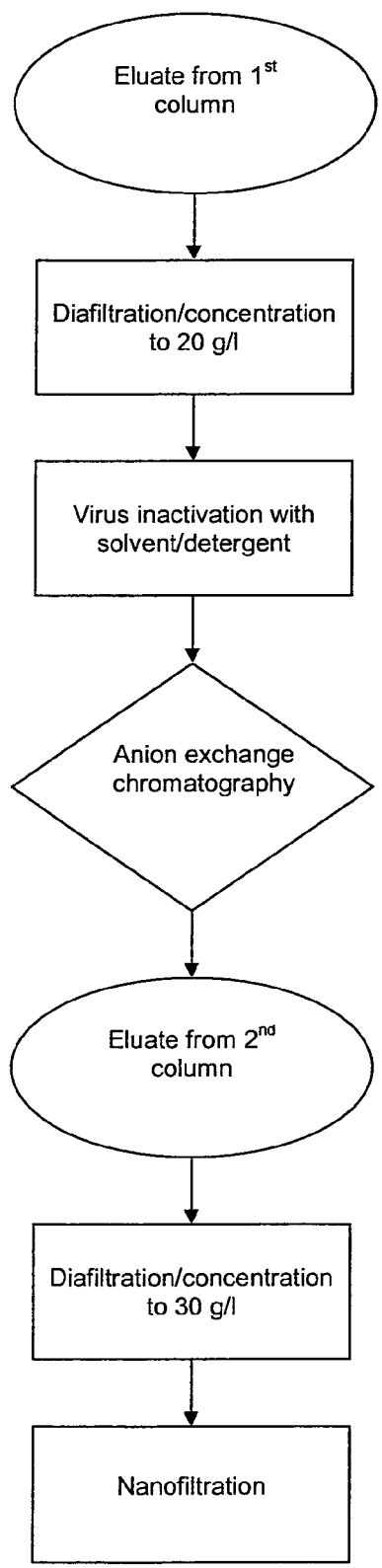
FIG. 2 shows the flowchart of a preferred embodiment of the method according to the invention, from the solution of IgG of intermediate purity after elution from the first "capture" chromatographic step on a strong cation exchange resin and up to the nanofiltering step following the second anion exchange chromatography step.
Figure 3:
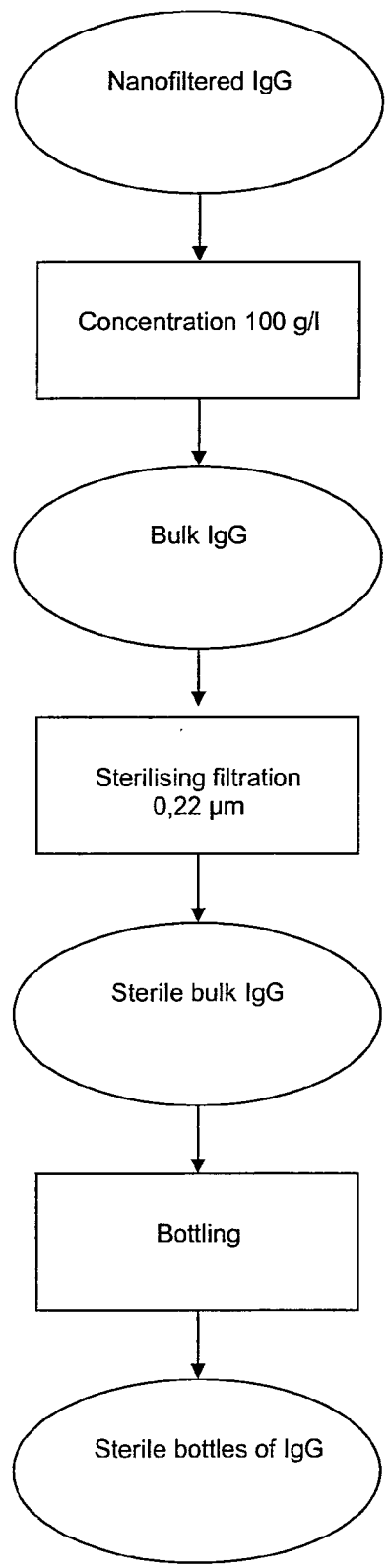
FIG. 3 shows the flowchart of the subsequent treatment of the IgG obtained by the method according to the invention, after the two ion exchange chromatography steps.

A particularly preferred embodiment of the purification process is shown in FIGS. 1, 2 and 3.

The present invention may be easier to understand in the light of the following examples of its embodiments.

EXPERIMENTAL PART

Example 1 a. Preparation of the Starting Material

The supernatant of fraction I (13 kg), obtained according to Cohn's method, was used as a starting material.

The pH of the sample was adjusted to 5.56 with acetic acid, then the sample was diluted approximately 3.5 times with water to achieve a final conductivity of 4 mS/cm, corresponding to that of the conditioning buffer in the cation exchange chromatography column. The diluted sample was filtered first through a depth filter and then through a clarifying filter.

b. Cation Exchange Chromatography

Cation exchange chromatography was performed on Capto S resin (manufactured by GE Healthcare) packed in a column 14 cm in diameter and 20 cm high. The column was conditioned with 50 mM sodium acetate buffer, pH 5.56, at a flow rate of 300 cm/h.

The diluted and filtered supernatant 1 was charged at a flow rate of 300 cm/h and at a charge of 40 mg IgG per ml of resin (total protein charge: 300 mg/ml of resin). After charging, the column was washed with seven column volumes of 50 mM sodium acetate buffer, pH 5.56. Elution was then performed with 50 mM sodium acetate buffer, pH 5.56, 600 mM sodium chloride, for a total of seven column volumes.

Table 1 shows the characteristics of the eluate after cation exchange chromatography.

TABLE 1

| Sample | % yield of IgG per step | IgG g/L | IgA mg/L | IgM mg/L | Albumin g/L | Transferrin g/L | Proteins g/L |
|---|---|---|---|---|---|---|---|
| Eluate Column Capto S | 86 ± 3 | 3.99 ± 0.58 | 111 ± 19 | 38.4 ± 7.7 | <0.36 | <0.088 | 7.23 ± 0.76 | c. Dialysis/Ultrafiltration

The eluate from ion exchange chromatography underwent dialysis/ultrafiltration using a cross flow filtering device and cassettes with a molecular cut-off of 100 KDa (Millipore or Pall).

Tris 20 mM pH 9.0 (at least six dialysis volumes) was used as a dialysis buffer and the sample was concentrated to obtain a protein concentration of 20 g/L.

d. Virus Inactivation with Solvent/Detergent Mixture

The dialysed sample, concentrated to 20 g/L, underwent virus inactivation by contact with a mixture of Triton X-100 (1% p/p) and Tri-n-butyl-phosphate (0.3% p/p) for 8 hours at a controlled temperature of 25° C.

After virus inactivation, the sample was clarified by filtering.

e. Anion Exchange Chromatography

Anion exchange chromatography was completed with Fractogel TMAE resin (manufactured by Merck) packed in a column 14 cm in diameter and 26 cm in height. The column was conditioned with Iris 20 mM buffer, pH 9.0, at a flow rate of 150 cm/h.

The inactivated and filtered sample was charged in the column with a protein charge of 30 mg per ml of resin, at a flow rate of 50 cm/h. After charging, the column was washed with 10 column volumes of Tris 20 mM buffer, pH 9.0, at a flow rate of 150 cm/h. Then elution was performed with the Tris 20 mM buffer, pH 9.0, and sodium chloride 75 mM, at a flow rate of 50 cm/h for a total of at least six column volumes.

Table 2 shows the characteristics of the immunoglobulin solution with a high grade of purity eluted from the cation exchange chromatography column:

TABLE 2

| Fraction | % yield of IgG per step | IgG g/L | IgA mg/L | IgM mg/L | Proteins g/L |
|---|---|---|---|---|---|
| Column eluate Fractogel TMAE | 82.5 ± 11.2 | 2.22 ± 0.08 | <0.2 | <0.1 | 2.28 ± 0.16 | f. Dialysis/Ultrafiltration

The sample underwent dialysis/ultrafiltration using a cross flow filtering device with cassettes with a molecular cut-off of 100 KDa (Millipore or Pall).

A 0.25 M glycine buffer with sodium chloride 0.6 g/L was used for the dialysis and formulation steps and the sample was concentrated to obtain a protein concentration of 30 g/L. The pH of the solution was adjusted to 4.0 with hydrochloric acid 1 N.

g. Nanofiltration

The protein solution concentrated to 30 g/L in buffer containing 0.25 M glycine and sodium chloride 0.6 g/L, pH 4.0, was filtered first through a sterilising grade filter and then through a virus removal filter with the porosity of 20 nm.

After removing viruses, the purified solution of IgG was concentrated to a final protein concentration of 100 g/L, then passed through a sterilising filter and bottled.

Example 2

For this example, Table 3 summarises the main characteristics of the end product obtained by applying the protocol described in example 1.

TABLE 3

| | Bach 1 | Bach 2 | Bach 3 | Mean |
|---|---|---|---|---|
| Purity (%) | 98.4 | 98.5 | 97.9 | 98.3 |
| monomers + dimers (%) | 99.492 | 99.897 | 99.21 | 99.53 |
| polymers (%) | 0.165 | 0.104 | 0.31 | 0.193 |
| fragments (%) | 0.342 | 0 | 0.48 | 0.274 |
| Distribution of the subclasses | | | | |
| IgG1 (g/l) | 36.7 | 55.71 | 52.73 | 48.38 |
| IgG2 (g/l) | 16.7 | 25.36 | 26.77 | 22.94 |
| IgG3 (g/l) | 1.46 | 4 | 4.24 | 3.23 |
| IgG4 (g/l) | 0.47 | 1.3 | 1.24 | 1 |
| IgA (mg/l) | 1.6 | 3.6 | 2 | 2.4 |
| IgM (mg/l) | <0.1 | <0.1 | <0.1 | <0.1 |
| Transferrin (g/l) | 0.135 | <0.088 | 0.23 | 0.151 |

Example 3

The solution of IgG with an intermediate purity obtained by implementing the protocol in example 1, items (a)-(d), was purified on Fractogel TMAE resin, as explained below:

e1. anion exchange chromatography: this was performed on Fractogel TMAE resin packed in column 2.6 cm in diameter and 21 cm high, and conditioned with a Tris 20 mM buffer, pH 9.0±0.1, NaCl 9 mM;

e2. charging of the solution of IgG of intermediate purity: the solution of IgG of intermediate purity obtained from the steps described in items (a)-(d) of example 1 was charged in the Fractogel TMAE column at a charge of 50 mg of protein per ml of resin and a flow rate of 50 cm/h;

e3. washing the Fractogel TMAE column: after completing the charge, the column was washed at a flow rate of 150 cm/h, with 10 column volumes of the conditioning buffer;

e4. IqG elution: the IgG were eluted at a flow rate of 150 cm/h. The five tests differed in the buffer used for elution, as shown in table 4. The eluates obtained in the various tests were converted into end products as explained in items (f) and (g) of example 1. Table 4 shows the % yields of each step in IgG and the levels of contaminants in the end products concentrated to 10% w/v.

TABLE 4

| Elution buffer | Buffer conductivity mS/cm | % yield of IgG per step | IgA mg/L | IgM mg/L | Transferrin g/L |
|---|---|---|---|---|---|
| Sodium phosphate 10 mM pH 6.2 | 1.0 | 95 | 2.53 | 0.89 | <0.08 |
| Sodium phosphate 15 mM, pH 6.2 | 1.3 | 99 | 6.61 | 0.95 | 0.42 |
| Sodium phosphate 50 mM, pH 6.2 | 4.0 | 97 | 18.53 | 2.04 | 26.21 |
| Sodium acetate 20 mM, pH 6.2 | 1.6 | 88 | 2.06 | 0.7 | <0.08 |
| MES 50 mM, pH 6.2 | 1.8 | 95 | 2.92 | <0.1 | 0.67 |

The invention claimed is:

1. A process for the production of IVIG, employing as starting material human plasma or an intermediate plasma fraction enriched in IgG, said process comprising the following chromatographic steps: a first chromatographic step, consisting in a step of "capture" of IgG, performed on a strong cation exchanger and a second chromatographic step, consisting in a step of "polishing", performed on a strong anion exchanger;

wherein the strong cation exchanger belongs to the category of strong exchanger characterized by $SO_3^-$ functional group; and wherein the strong anion exchanger has quaternary ammonium groups as exchanger groups;

wherein between the two chromatographic steps is performed at least a step of viral inactivation performed by means of a solvent-detergent treatment;

wherein subsequently after the second chromatographic step the solution containing IVIG is subjected to a viral inactivation step by means of nanofiltration;

wherein strong cation exchanger is charged with 20-60 mg of IgG/ml of resin and wherein the conditioning, charging and washing steps are performed employing a 25-75 mM buffer at pH 5.4-5.7 while the elution is performed using a buffer having 0.25-1 M sodium chloride concentration;

wherein the strong anion exchanger is charged with 20-60 mg of protein/ml of resin and wherein the conditioning, charging and washing steps are performed employing a 10-30 mM buffer, pH 9.0±0.5, NaCl 8-10 mM while the elution is performed or using an increased ionic strength or by means of pH variation; when the elution is performed using an increased ionic strength it is employed a buffer having a conductibility of 9.5-10.5 mS/cm and pH 9.0±0.5; when the elution is performed by means of pH variation, it is employed a buffer having a a conductibility of 1-1.5 mS/cm, and pH 6-7.

2. Process according to claim 1 wherein as starting material is employed criosurnatant or surnatant of Cohn fraction I.

3. Process according to claim 2 wherein before the chromatographic step on strong cation exchanger the supernatant is subjected to pH correction at a value 5.4-5.7, and then dilution with water to conductibility of 3.5-4.5 mS/cm.

* * * * *